United States Patent [19]
Blaschka et al.

[11] Patent Number: 5,513,252
[45] Date of Patent: Apr. 30, 1996

[54] DENTAL X-RAY DIAGNOSTICS INSTALLATION

[75] Inventors: Eriks Blaschka, Weinheim; Ulrich Schulze-Ganzlin, Lorsch, both of Germany

[73] Assignee: Siemens Aktiengesellschaft, Munich, Germany

[21] Appl. No.: 347,432

[22] PCT Filed: Apr. 27, 1993

[86] PCT No.: PCT/DE93/00368

§ 371 Date: Nov. 28, 1994

§ 102(e) Date: Nov. 28, 1994

[87] PCT Pub. No.: WO93/25059

PCT Pub. Date: Dec. 9, 1993

[30] Foreign Application Priority Data

Jun. 1, 1992 [DE] Germany ............ 42 18 020.1

[51] Int. Cl.$^6$ ................................. G01N 23/04
[52] U.S. Cl. ............ 378/98.8; 378/98.2; 250/370.07
[58] Field of Search ............ 378/98.8, 97, 98, 378/98.2, 98.3, 19, 98.5; 250/354.1, 370.07, 370.09

[56] References Cited

U.S. PATENT DOCUMENTS 4,901,336  2/1990  Nishiki ................................. 378/98.8

FOREIGN PATENT DOCUMENTS 0415075    3/1991  European Pat. Off. .
WO92/22188 12/1992  WIPO .

*Primary Examiner*—Constantine Hannaher
*Assistant Examiner*—Don Wong
*Attorney, Agent, or Firm*—Hill, Steadman & Simpson

[57] ABSTRACT

In a dental x-ray diagnostics installation that includes an x-ray radiator, an image detector arranged diametrically relative thereto a CCD following the subject to be transirradiated in radiation direction, control electronics with a control part for driving the image detector, an image processing unit that edits the signals acquired from the image detector, and an operating device with which the x-ray radiator can be switched on and off, the image detector is continuously read out with a clock generator and the incoming data read from the detector are constantly subjected to a threshold check. The image detector is operated in a read-out mode when the x-ray radiator is switched off and is switched into an exposure mode given the presence of radiation and the upward transgression of a defined threshold, and vice versa.

1 Claim, 2 Drawing Sheets

DENTAL X-RAY DIAGNOSTICS INSTALLATION

BACKGROUND OF THE INVENTION

1. Field of the Invention

The invention is directed to a dental x-ray diagnostics installation of the type having an x-ray radiator, a CCD image detector arranged diametrically relative thereto and following the subject to be transirradiated in a radiation propagation direction, control electronics with a control unit which drives the image detector, an image processing unit which edits the signals acquired from the image detector and supplies them to an image presentation unit, and an operating device with which the x-ray radiator can be switched on and off.

2. Description of the Prior Art

European Application No. 0 415 075 discloses an x-ray diagnostics installation of the above type. In order, in particular, to make the connecting cable between x-ray radiator and the control electronics with the image processing unit dispensable, a radiation-sensitive sensor is arranged in the reception area of the image detector in this known x-ray diagnostics installation. According to an advantageous development of this known installation, the sensor can also be arranged inside the area of the image detector.

WO-A-9-222 188, which does not have prior publication, discloses an apparatus wherein an image detector is employed instead of a film that is sensitive to x-rays; in this apparatus, however, image data are not clocked and evaluated; on the contrary, the static signals that correspond to the supply current flowing to and from the CCD sensor are continuously subjected therein to a threshold check.

SUMMARY OF THE INVENTION

It is an object of the present invention to provide an x-ray diagnostics installation of the type generally described above which does not require the use of a radiation-sensitive sensor disposed in the reception area of the image detector.

The above object is achieved in accordance with the principles of the present invention in a dental x-ray diagnostics installation of the type generally described above, wherein a clock generator is connected to the CCD image detector for continuously reading out the CCD image detector to obtain image data, and wherein the image data are continuously subjected to a threshold comparison to determine whether the x-ray radiator is currently activated, and is emitting x-rays, or whether the x-ray radiator has been deactivated. When the x-ray radiator is activated, as determined by the threshold comparison, the clock generator operates the CCD detector in an exposure mode, and when the x-ray radiator is deactivated, the clock generator operates the image detector in a read-out mode.

Because the image detector is continuously read out and the incoming values are thus continuously subjected to a threshold check that immediately recognizes the presence of a radiation and correspondingly activates the control electronics, the radiation-sensitive sensor provided in known devices in the area of the image detector can be forgone. The control electronics is automatically switched on as soon as the x-ray radiator is activated via the operating device.

DESCRIPTION OF THE DRAWINGS

An exemplary embodiment of the invention shall be set forth in greater detail below with reference to the drawings.

DESCRIPTION OF THE PREFERRED EMBODIMENTS

Figure 1:
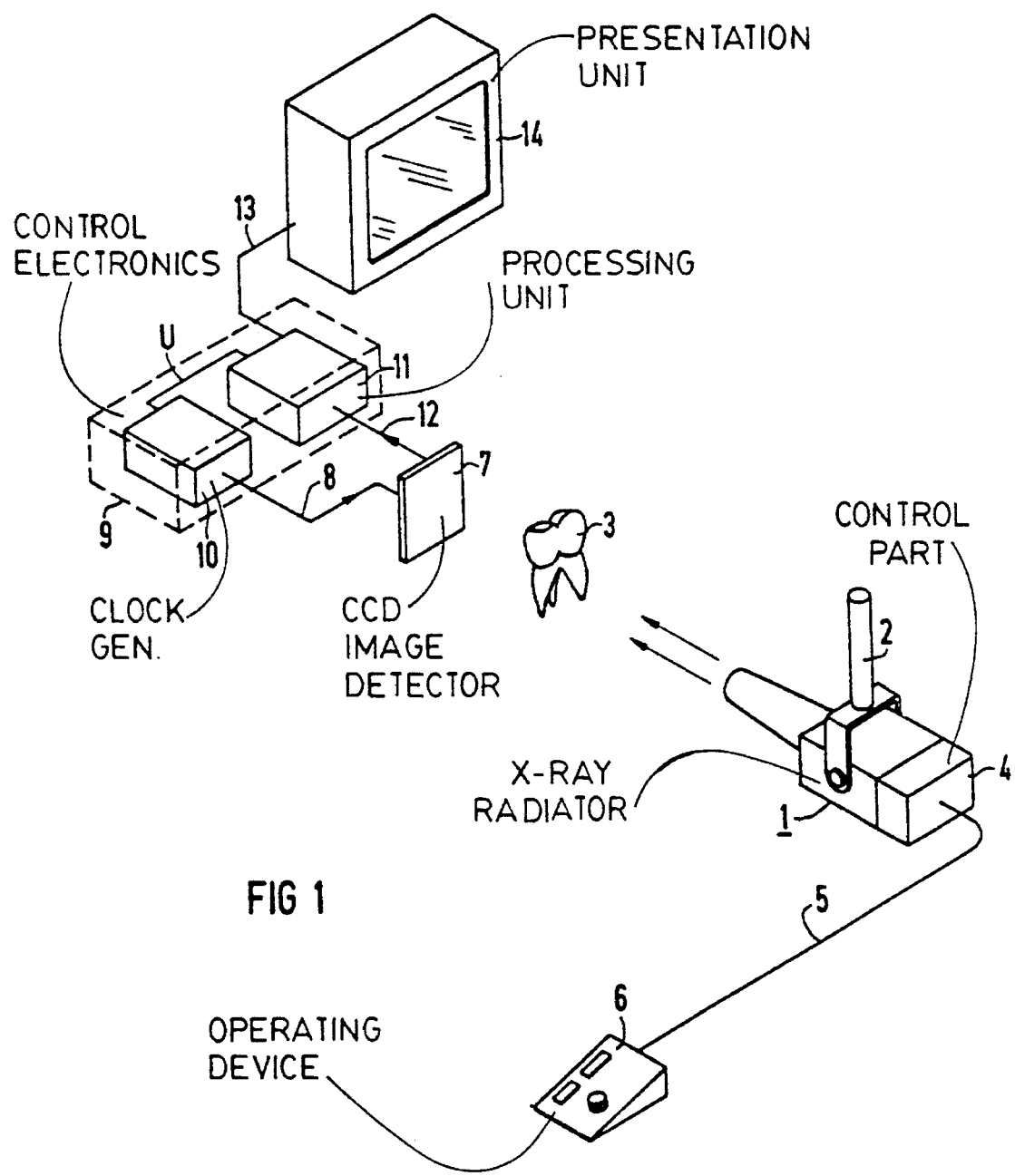
FIG. 1 is an overview of the x-ray diagnostics installation of the invention.

The diagnostics installation shown in FIG. 1 includes an x-ray radiator 1 that contains an x-ray tube (not referenced in detail) with a high-voltage generator operable in a known way, held in a suitable way with a holder 2 such that it can be aligned to the subject 3 (tooth or jaw of a patient) to be transirradiated. In the case of an intraoral diagnostics installation, the holder 2 can be composed in a known way of a floor or ceiling stand at which the x-ray radiator 1 is adjustable in height, slope and swivel direction. In the case of a panorama x-ray diagnostics installation, the holder also contains the image detector (referenced 7) that is arranged following the transirradiated subject in the radiation propagation direction.

The x-ray radiator 1 further contains a control part 4 that is connected via a control cable 5 to an operating device 6 with which specific exposure values such as tube voltage, exposure time, can be set.

An image detector 7 is arranged lying diametrically opposite the x-ray radiator and following the subject 3 to be transirradiated in the radiation propagation direction; in the case of an intraoral x-ray diagnostics installation, this image detector 7 can be placed in the patient's mouth. The image detector is a CCD detector that is connected via a control cable 8 to a clock generator 10 that is part of a control electronics generally referenced 9. This control electronics 9 also contains an image processing unit 11 that is connected via a control line 12 to the CCD detector 7 and that correspondingly edits, stores and amplifies the signals acquired from the detector and finally supplies them via a line 13 to an image presentation unit 14, for example a monitor.

Figure 2:
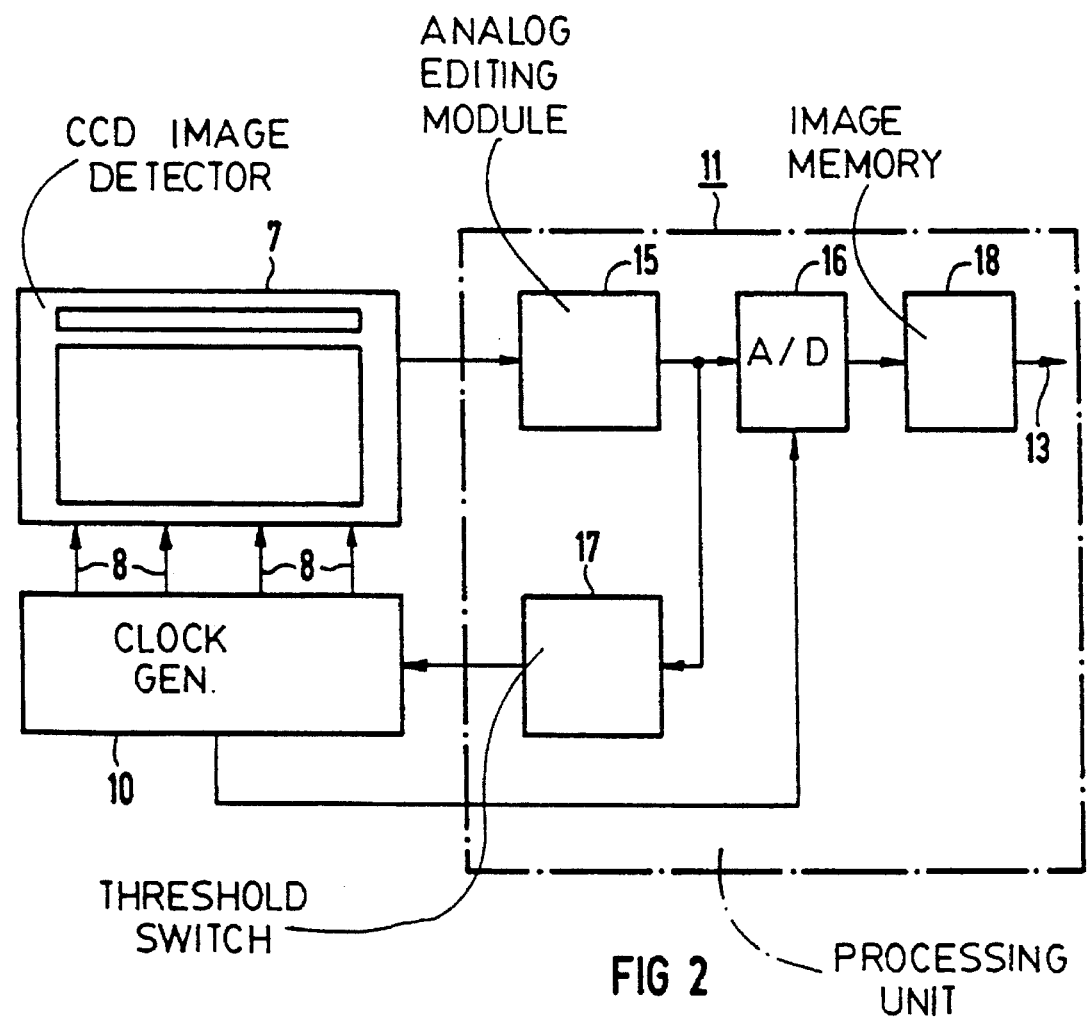
FIG. 2 is a block circuit diagram of the diagnostics installation of the invention.

Inventively, the CCD detector 7 is continuously read out via the clock generator 10, whereby the incoming image data read out from the CCD detector 7 are constantly subjected to a threshold check in a threshold switch 17. In what is referred to as the standby condition wherein the x-ray radiator 1 is deactivated, the image detector 7 is operated in a read-out mode that allows incident x-rays to be detected and registered. As soon as the x-ray radiator is switched on via the operating device 6, a voltage corresponding to the incident radiation is generated at the image detector. As shown in FIG. 2, after analog editing in a module 15, the edited analog signal supplied both to an A/D converter 16 and to a threshold switch 17. When the threshold defined in the threshold switch 17 (such as a signal level) is upwardly exceeded, the clock generator 10 switches into the exposure mode. The images thereby produced by integration of the charges can be stored in the image memory 18 and are supplied as display signals to the image presentation unit 14 for playback (FIG. 1). Correspondingly, the end of the exposure is recognized and a switch is then made back into the read-out mode. The switching ensues in a relatively short time; dependent on the rate of the clock, the chronological duration until the maximum value of the output voltage is reached amounts to between approximately 150 and 700 µs given an assumed clock frequency of 4 MHz through 1 MHz.

So that the detection of the radiation also ensues reliably under unfavorable circumstances, for example even given partial coverage of the CCD detector 7 by fillings, the threshold of the threshold switch 17 is defined such that a triggering lies far below the maximum value. The response time in the control case can thereby be even shorter than cited above.

Although modifications and changes may be suggested by those skilled in the art, it is the intention of the inventor to embody within the patent warranted hereon all changes and modifications as reasonably and properly come within the scope of his contribution to the art.

We claim:

1. A dental x-ray diagnostics installation comprising:

an x-ray source;

x ray source control means for selectively activating said x-ray source to cause said x-ray source to emit x-rays, and for deactivating said x-ray source;

an image memory;

a CCD image detector disposed opposite said x-ray source;

clock generator means for operating said CCD x-ray image detector in an exposure mode wherein said CCD x-ray image detector integrates charge produced by x-rays emitted by said x-ray source which are incident on said CCD image detector to produce x-ray image data, and in a read-out mode wherein said x-ray image data are read from said CCD x-ray image detector and entered into said image memory;

threshold means continuously supplied with said x-ray image data for continuously comparing said x-ray image data to a threshold which is exceeded when said x-ray source is activated by said x-ray source control means and for causing said clock generator means to operate said CCD x-ray image detector in said exposure mode when said threshold is exceeded and otherwise to operate said CCD x-ray image detector in said read-out mode, said threshold means being unconnected to said x-ray source control means;

means including said image memory for processing said x-ray image data to produce display signals therefrom; and means supplied with said display signals for presenting a visual display of said x-ray image data.

* * * * *